United States Patent [19]

Conrow et al.

[11] 4,369,191

[45] Jan. 18, 1983

[54] NAPHTHALENETETRAYLTETRAKIS(SULFONYLIMINO)-TETRABENZENE DI- AND TRICARBOXYLIC ACIDS

[75] Inventors: Ransom B. Conrow, Pearl River; Seymour Bernstein, New City, both of N.Y.

[73] Assignee: American Cyanamid Company, Stamford, Conn.

[21] Appl. No.: 286,737

[22] Filed: Jul. 27, 1981

[51] Int. Cl.³ ................... C07C 143/80; A61K 31/19
[52] U.S. Cl. ................................... 424/319; 562/427
[58] Field of Search ..................... 562/427; 424/319

[56] References Cited

U.S. PATENT DOCUMENTS 4,087,613  5/1978  Conrow .......................... 560/10
4,266,077  5/1981  Conrow .......................... 562/427

Primary Examiner—Robert Gerstl
Attorney, Agent, or Firm—Anne M. Rosenblum

[57] ABSTRACT

Naphthalenetetrayltetrakis(sulfonylimino)tetrabenzene di- and tricarboxylic acids and salts thereof useful as complement inhibitors and the process of making such compounds.

9 Claims, No Drawings

NAPHTHALENETETRAYLTETRAKIS(SULFONYLIMINO)-TETRABENZENE DI- AND TRICARBOXYLIC ACIDS

BACKGROUND OF THE INVENTION

1. Field of the Invention

The present invention relates to novel naphthalenetetrayltetrakis(sulfonylimino) tetrabenzene di- and tricarboxylic acids and salts thereof and their use as inhibitors of the complement system of warm-blooded animals. The invention further concerns a process for making such compounds.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W.H.O. 39: 935 (1968); Annu. Rev. Med. 19: 1 (1968); Johns Hopkins Med. J. 128: 57 (1971); Harvey Lect. 66: 75 (1972); N. Engl. J. Med. 287: 452, 489, 454, 592, 642 (1972); Sci. Am. 229 (5): 54 (1973); Fed. Proc. 32: 134 (1973); Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant Rev.: 32 (1976); "Complement: Mechanisms and Functions," Prentice-Hall, Englewood Cliffs, N.J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1659 (1977); Harvey Lect. 72: 139 (1976-1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestion regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 15: 813 (1978); J. Biol. Chem. 254: 9908 (1979).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anti-complementary effect, Br. J. Exp. Pathol. 33: 327 (1952). German Pat. No. 2,254,893 or South African Patent No. 727,923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem. 47: 547 (1969); J. Immunol. 104: 279 (1970); J. Immunol. 106: 241 (1971); J. Immunol. 111: 1061 (1973); Biochim. Biophys. Acta 317: 539 (1973); Life Sci. 13: 351 (1973); J. Immunol. 113: 584 (1974); Immunology 26: 819 (1974); J. Med. Chem. 17: 1160 (1974); Biochim.

Biophys. Res. Comm. 67: 225 (1975); Ann. N.Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci. 66: 1367 (1977); Chem. Pharm. Bull. 25: 1202 (1977); Biochim. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979); Biochim. Biophys. Acta 611: 196 (1980); and J. Med. Chem. 23: 240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972); 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosanpolysulfoester has an anticomplementary activity on human serum, both in vitro and in vivo, as judged by the reduction in total hemolytic complement activity, Pathol. Biol. 25: 33; 25 (2): 105; 25 (3): 179 (1977).

SUMMARY OF THE INVENTION

It has now been discovered that naphthalenetetrayltetrakis(sulfonylimino) tetrabenzene di- and tricarboxylic acids and salts interact with the complement reaction sequence, thereby inhibiting complement activity in body fluids.

This invention also concerns a method of inhibiting the complement system in a body fluid which comprises subjecting body fluid complement to the action of an effective complement inhibiting amount of the above-identified compounds. This invention further deals with a method of inhibiting the complement system in a warm-blooded animal which comprises administering to said animal an effective complement inhibiting amount of the above described compounds.

DETAILED DESCRIPTION OF THE INVENTION

In accordance with the present invention, there is provided novel compounds represented by the following generic formula:

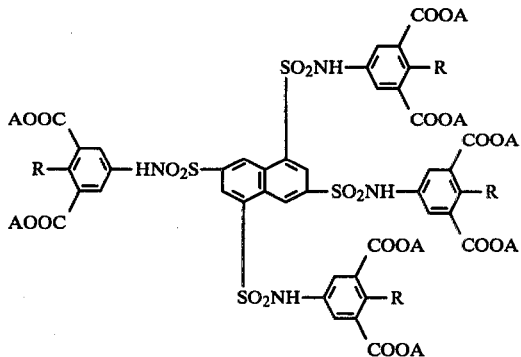

wherein R is selected from the group consisting of hydrogen and —COOA; and A is a nontoxic pharmaceutically acceptable cation salt, wherein the salt forming moiety is selected from the group consisting of alkali metal, alkaline earth metal, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$).

Particularly preferred compounds of this invention which are of major interest as complement inhibitors include the following:

5,5′,5″,5‴-[1,3,5,7-Naphthalenetetrayltetrakis(sulfonylimino)]tetraisophthalic acid, octasodium salt 5,5′,5″,5‴-[1,3,5,7-Naphthalenetetrayltetrakis(sulfonylimino)]tetra-1,2,3-benzenetricarboxylic acid, dodecasodium salt Additionally, the instant invention involves a method of inhibiting the complement system in a body fluid, such as blood serum, which comprises subjecting body fluid complement to the action of an effective complement inhibiting amount of a compound of the above formula. Body fluids can include blood, plasma, serum, synovial fluid, cerebrospinal fluid, or pathological accumulations of fluid such as pleural effusion, etc. This invention further concerns a method of inhibiting the complement system in a warm-blooded animal which comprises administering to said warm-blooded animal an effective complement inhibiting amount of a compound of the above formula.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having non-immunologic diseases such as paroxysmal nocturnal hemoglobinurea, hereditary angioneurotic edema (such as Suramin Sodium, etc.) and inflammatory states induced by the action of bacterial or lysosomal enzymes on the appropriate complement components as, for example, inflammation following coronary occlusion. They may also be useful in the treatment of transplant rejection and ulcers and as blood culture and transport mediums.

The compounds of the present invention may be prepared according to the following flowchart.

Flowchart

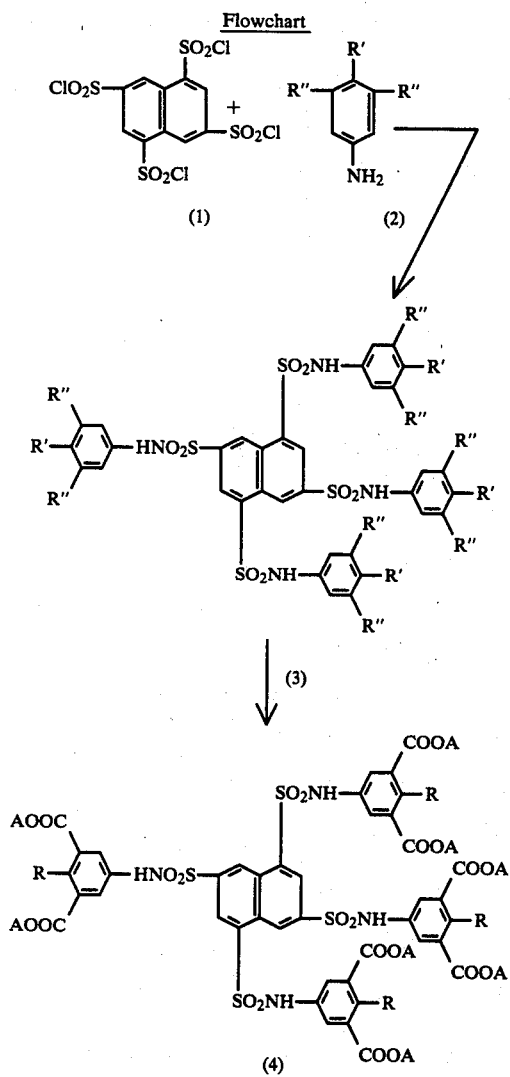

General Procedure

In accordance with the preceding flowchart, 1,3,5,7-naphthalenetetrasulfonyl chloride (1) and a compound (2) wherein R' is hydrogen or phenyl carboxylate and R'' is methoxyethyl carboxylate or phenyl carboxylate in a solvent such as pyridine is reacted for several hours to produce (3) which is extracted in dichloromethane. The compound is then converted by conventional procedures to its acid or salt (4) where R is hydrogen or —COOA and A is hydrogen or a pharmaceutically acceptable cation salt such as sodium using sodium hydroxide or sodium carbonate.

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, thin-layer chromatography, distillation, etc. Also, it should be appreciated that when typical reaction conditions (e.g., temperatures, mole ratios, reaction times) have been given, the conditions which are both above and below these specified ranges can also be used, though generally less conveniently.

The term "pharmaceutically acceptable salts" refers to those salts of the parent compound which do not significantly or adversely affect the pharmaceutical properties (e.g., toxicity, effectiveness, etc.) of the parent compound. The salts of the present invention which are pharmaceutically acceptable include the alkali metals (e.g., sodium, potassium, etc.); alkaline earth metals (e.g., calcium, etc.); ammonia; and substituted ammonia selected from the group consisting of trialkylamine ($C_1$–$C_6$), piperidine, pyrazine, alkanolamine ($C_2$–$C_6$) and cycloalkylamine ($C_3$–$C_6$).

The term "trialkylamine ($C_1$–$C_6$)" defines those amines having three aliphatic fully saturated hydrocarbon substituents containing 1 to 6 carbon atoms either linearly or branched. Typically, these amines are trimethylamine, triethylamine, tripropylamine, dimethylethylamine, dimethyl-1-propylamine, etc. The term "alkanolamine ($C_2$–$C_6$)" refers to the above-defined trialkylamines additionally substituted with at least one and not more than three hydroxy groups on at least two of the alkyl hydrocarbon chains. Such amines are, for example, triethanolamine, tripropanolamine, etc. The term "cycloalkylamine ($C_3$–$C_6$)" is defined as the 3 to 6 fully saturated carbocyclic moieties such as cyclopropyl, methylcyclobutyl, cyclopentyl, cyclohexyl, etc.

As used hereinabove and below unless expressly stated to the contrary, all temperatures and temperature ranges refer to the centigrade system and the terms "ambient" or "room temperature" refer to about 20° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

A further understanding of the invention can be obtained from the following non-limiting Preparations and Examples.

EXAMPLE 1

5,5',5'',5'''-[1,3,5,7-Naphthalenetetrayltetrakis(sulfonylimino)]tetraisophthalic acid, octasodium salt A mixture of 100 g of 5-nitroisophthaloyl dichloride, 100 g of 2-methoxyethanol and 400 ml of acetonitrile is heated on a steam bath at boiling for 15 minutes. The mixture is cooled to room temperature and poured into 2 liters of cold water with vigorous stirring. The solid is collected by filtration, partially air dried and saved. The filtrate is extracted with benzene. The extract is washed successively with water, dilute aqueous sodium bicarbonate and water and dried over sodium sulfate. Evaporation gives a mixture of crystals and oil which are combined with the first solid and dissolved in 580 ml of hot ethanol. The solution is neutralized with 5 N sodium hydroxide and then diluted slowly with 450 ml of water. This solution is allowed to crystallize in a cold room over a period of 3½ hours giving 96.1 g of solid. This solid is recrystallized as above from 450 ml of ethanol and 350 ml of water giving 78.6 g of 5-nitro-di(2-methoxyethyl)isophthalate. A mixture of 78.6 g of 5-nitro-di(2-methoxyethyl)isophthalate, 150 ml of ethyl acetate and 1.5 g of 10% palladium on carbon catalyst is hydrogenated on a Parr shaker for one hour. The mixture is filtered through celite and the cloudy filtrate is dried over sodium sulfate and evaporated to a solid. This solid is dissolved in 300 ml of benzene, 120 ml of hexane is added and the solution is allowed to crystallize overnight giving 56.6 g of 5-amino-di(2-methoxyethyl)isophthalate as colorless crystals.

To 100 ml of 30% fuming sulfuric acid at 200° C., is added 25 g of 1,5-naphthalenedisulfonic acid disodium salt. The mixture is refluxed at 180°–185° C. for 18 hours then cooled to 50°–60° C. and filtered, giving 25.6 g of 1,3,5,7-naphthalenetetrasulfonic acid as a tan solid. The entire 25.6 g is added to 200 ml of thionyl chloride and then 2.0 ml of dimethylformamide are added. The mixture is warmed gently until hydrogen chloride is evolved, then heated until bubbling, then allowed to stand at room temperature for 1¾ hours and finally refluxed for 3 hours. The mixture is filtered while warm and the filtrate is evaporated to 20 ml. The solid is collected by filtration and washed with dichloromethane and ether, giving 3.0 g of 1,3,5,7-naphthalenetetrasulfonyl chloride as a colorless powder.

To a solution of 5.94 g of 5-amino-di(2-methoxyethyl)isophthalate in 25 ml of pyridine is added 2.6 g of 1,3,5,7-naphthalenetetrasulfonyl chloride. The mixture is stirred at room temperature and then on a steam bath for 35 minutes to effect solution, then cooled, poured into 100 ml of water and allowed to stand overnight. The resulting oil is recovered by decantation and dissolved in 100 ml of dichloromethane. This solution is washed with 50 ml of 2 N hydrochloric acid then with dilute aqueous sodium chloride. The organic phase is filtered through celite, partially dried over a mixture of sodium sulfate and charcoal, refiltered through celite and evaporated to a solid. This solid is triturated with ether and evaporated to dryness. This solid is dissolved in 100 ml of methanol:dichloromethane (1:1) and boiled with the addition of methanol until all of the dichloromethane is removed. Some initial precipitate is removed by filtration. The filtrate is allowed to crystallize after concentration to 50 ml. The solid is collected, dissolved in 100 ml of methanol:dichloromethane (1:1) and stirred over sodium carbonate. The mixture is filtered through celite and allowed to crystallize overnight giving 4.4 g of a solid. This solid and its attendant filtrate are combined, dichloromethane is added until solution is obtained and this is evaporated to a glass. This glass is dissolved in 50 ml of dichloromethane and filtered through 30 g of an acid silicate of magnesium, using as eluting solvents two 100 ml portions of dichloromethane followed by 200 ml of 5% methanol in dichloromethane. The combined 5.85 g of solid is dissolved in 20 ml of tetrahydrofuran, filtered through celite and diluted with 80 ml of ether. The resulting solid is collected by filtration and washed with ether, giving 5.15 g of 5,5',5'',5'''-[1,3,5,7-naphthalenetetrayltetrakis(sulfonylimino)]tetraisophthalic acid, octakis(2-methoxyethyl) ester.

A 5.0 g portion of the above ester in 24 ml of 2 N sodium hydroxide is stirred for one hour at room temperature and then neutralized with 1.41 ml of acetic acid. The solution is then diluted with 150 ml of ethanol and the solid is collected by filtration, washed with ethanol and ether and dried at 110° C., giving 4.32 g of the desired product as an orange powder.

EXAMPLE 2

5,5',5'',5'''-[1,3,5,7-Naphthalenetetrayltetrakis(sulfonylimino)]tetra-1,2,3-benzenetricarboxylic acid, dodecasodium salt To a solution of phenol in 305 ml of pyridine is added 69.05 g of 5-nitro-1,2,3-benzenetricarboxyl chloride with water bath cooling. The solution is heated on a steam bath for one hour, cooled and poured into 1500 ml of ice water with vigorous stirring until the oily precipitate solidifies. The solid is collected by filtration, dissolved in dichloromethane, dried over sodium sulfate, filtered and concentrated with the addition of ethanol until a solid precipitates, then allowed to stand overnight. The solid is collected by filtration, washed with ethanol, then ether and dried in vacuo, giving 76 g of 5-nitro-1,2,3-benzenetricarboxylic acid triphenyl ester.

A 48.3 g portion of the above compound, 5.0 g of 10% palladium on carbon catalyst and 300 ml of tetrahydrofuran are mixed and hydrogenated for 1¼ hours. The mixture is filtered through celite and the filtrate is evaporated to a yellow glass. The glass is dissolved in 100 ml of dichloromethane and boiled with the addition of 400 ml of ethanol until all of the dichloromethane is removed. The mixture is allowed to crystallize and the solid is collected by filtration and washed with ethanol and ether giving 38.0 g of 5-amino-1,2,3-benzenetricarboxylic acid triphenyl ester.

To a solution of 36.27 g of 5-amino-1,2,3-benzenetricarboxylic acid triphenyl ester in 150 ml of pyridine at room temperature is added 12.0 g of 1,3,5,7-naphthalenetetrasulfonyl chloride. The mixture is stirred at room temperature for one hour, heated at 55°–75° C. for 2 hours and then poured into a mixture of 700 ml of water and 140 ml of concentrated hydrochloric acid with vigorous stirring. The mixture is extracted with 500 ml of dichloromethane, filtered and the solid is washed with water and dichloromethane then dried giving 32.4 g of crude product. This product is dissolved in 150 ml of acetone, filtered through celite and diluted with 300 ml of dichloromethane. The mixture is allowed to crystallize in a refrigerator. The solid is collected by filtration, washed with acetone:dichloromethane (1:2) and air dried. Two more crops are recovered by essentially the same procedure. The combined solids are refluxed in 200 ml of acetone, then in a mixture of 700 ml of acetonitrile and 350 ml of methanol. The solid is recovered by filtration and dried at 110° C. overnight giving 21.45 g of 5,5',5'',5'''-[1,3,5,7-naphthalenetetrayltetrakis(sulfonylimino)]tetra-1,2,3-benzenetricarboxylic acid, dodecaphenyl ester.

A 10.951 g portion of the above dodecaphenyl ester is added to 85.0 ml of 2 N sodium hydroxide. The mixture is stirred at room temperature for one hour and then neutralized with 6.29 ml of acetic acid. The mixture is concentrated in vacuo to about 65 ml and then poured into 550 ml of absolute ethanol with vigorous stirring. The solid is collected by filtration, washed with ethanol and ether and then dissolved in 65 ml of water. The solution is filtered and the filtrate is adjusted to pH 7.4 with 1 N sodium hydroxide and poured into 750 ml of absolute ethanol. A 7.5 g portion of sodium acetate trihydrate is added and the mixture is stirred. The gum is collected by decantation, triturated with ethanol until solid and collected by filtration. This solid is dissolved in 65 ml of water, adjusted to pH 7.4 with acetic acid and poured into 1500 ml of ethanol with vigorous stirring. A 5.0 g portion of sodium acetate trihydrate is added and stirring is continued for 2 hours. The mixture is filtered and the solid is washed with ethanol and ether and dried at 110° C. over phosphorus pentoxide, giving 8.2 g of the desired product as an orange powder.

EXAMPLE 3

Preparation of Compressed Tablet

| Ingredient | mg/Tablet |
|---|---|
| Active Compound | 0.5–500 |
| Dibasic Calcium Phosphate NF | qs |
| Starch USP | 40 |
| Modified Starch | 10 |
| Magnesium Stearate USP | 1–5 |

EXAMPLE 4

Preparation of Compressed Tablet - Sustained Action

| Ingredient | mg/Tablet |
|---|---|
| Active Compound as Aluminum Lake*, Micronized | 0.5–500 (as acid equivalent) |
| Dibasic Calcium Phosphate NF | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 5

Preparation of Hard Shell Capsule

| Ingredient | mg/Capsule |
|---|---|
| Active Compound | 0.5–500 |
| Lactose, Spray Dried | qs |
| Magnesium Stearate | 1–10 |

EXAMPLE 6

Preparation of Oral Liquid (Syrup)

| Ingredient | % W/V |
|---|---|
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 7

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 8

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |

Preparation of Oral Suspension (Syrup) -continued

| Ingredient | % W/V |
|---|---|
| Methyl Paraben USP | 0.18 |
| Propyl Paraben USP | 0.02 |
| Liquid Sugar | 75.0 |
| Purified Water qs ad | 100.0 |

EXAMPLE 9

Preparation of Injectable Solution

| Ingredient | % W/V |
|---|---|
| Active Compound | 0.05–5 |
| Benzyl Alcohol NF | 0.9 |
| Water for Injection | 100.0 |

EXAMPLE 10

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 11

Preparation of Intra-Articular Product

| Ingredient | Amount |
|---|---|
| Active Compound | 2–20 mg |
| NaCl (physiological saline) | 0.9% |
| Benzyl Alcohol | 0.9% |
| Sodium Carboxymethylcellulose | 1.5% |
| pH adjusted to 5.0–7.5 | |
| Water for Injection qs ad | 100% |

EXAMPLE 12

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol NF | 0.9 |
| HCl to pH 6–8 | qs |
| Water for Injection qs ad | 100.0 |

EXAMPLE 13

Preparation of Dental Paste

| Ingredient | % W/W |
|---|---|
| Active Compound | 0.05–5 |
| Zinc Oxide | 15 |
| Polyethylene Glycol 4000 USP | 50 |
| Distilled Water qs | 100 |

EXAMPLE 14

Preparation of Dental Ointment

| Ingredient | % W/W |
|---|---|
| Active Compound | 0.05–5 |
| Petrolatum, White USP qs | 100 |

EXAMPLE 15

Preparation of Dental Cream

| Ingredient | % W/W |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 16

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 17

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs. | 100 |

EXAMPLE 18

Preparation of Spray Lotion (Non-aerosol)

| Ingredient | % W/W |
|---|---|
| Active Compound | 0.05–5 |
| Isopropyl Myristate | 20 |
| Alcohol (Denatured) qs | 100 |

EXAMPLE 19

Preparation of Buccal Tablet

| Ingredient | mg/Tablet |
|---|---|
| Active Ingredient | 3.25 |
| 6 × Sugar | 290.60 |
| Acacia | 14.53 |
| Soluble Starch | 14.53 |
| F.D. & C. Yellow No, 6 Dye | 0.49 |
| Magnesium Stearate | 1.60 |

-continued
Preparation of Buccal Tablet

| Ingredient | mg/Tablet |
|---|---|
|  | 325.00 |

The final tablet will weigh about 325 mg and may be compressed into buccal tablets in flat faced or any other tooling shape convenient for buccal administration.

EXAMPLE 20

Preparation of Lozenge

| Ingredient | g/Lozenge |
|---|---|
| Active Ingredient | 0.0140 |
| Kompact ® Sugar (Sucrest Co.) | 0.7138 |
| 6 × Sugar | 0.4802 |
| Sorbital (USP Crystalline) | 0.1038 |
| Flavor | 0.0840 |
| Magnesium Stearate | 0.0021 |
| Dye | qs |
| Stearic Acid | 0.0021 |
|  | 1.4000 |

The ingredients are compressed into ⅝" flat based lozenge tooling. Other shapes may also be utilized.

The compounds of the present invention may be administered internally, e.g., orally, intra-anticularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form," as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention is indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3–C9 inhibitor)—This test determines the ability of the late components of human complement (C3–C9) to lyse EAC 142 in the presence of appropriate dilutions of the test compound. An active inhibitor protects EAC 142 from lysis by human C3–C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Cap 50 Test—Here, appropriate amounts of the test compound are added to a pool of guinea pig serum in vitro, after which the undiluted serum capillary tube assay of U.S. Pat. No. 3,876,376 is run. The concentration of compound inhibiting 50% is reported; and (v) Guinea Pig Intraperitoneal Test (GPIP)—Guinea pigs weighing about 300 g are dosed intraperitoneally (i.p.) with 200 mg/kg of the test compound dissolved in saline and adjusted to pH 7–8. Approximately 0.4 ml blood samples, taken by orbital sinus puncture 30 minutes and one hour after injections, are collected directly into centrifuge tubes; 5 ml blood samples, taken by decapitation 2 hours after injection are collected directly into diSPo ® beakers. The samples were allowed to clot, centrifuged, and the resultant sera were assayed for complement activity using the capillary complement assay. Percent inhibition is calculated by comparison with simultaneous controls. The results of the GPIP appear in Table I together with results of Test Code 026, 035, 036 and Cap 50. Table I shows that the principal compounds of the invention possess highly significant in vitro and in vivo complement inhibiting activity in warm-blooded animals.

TABLE I

| | Biological Activities | | | | | | |
|---|---|---|---|---|---|---|---|
| | In vitro Activity | | | | In vivo Activity (Guinea Pigs) | | |
| | C1 026* | C-Late 035* | C-Shunt Inhibition 036* | | % Inhibition Intraperitoneal Time (Minutes) | | |
| Compound | Wells | Wells | Wells | Cap 50 | 30 | 60 | 120 |
| 5,5′,5″,5‴-[1,3,5,7-Naphthalenetetrayl-tetrakis(sulfonylimino)]tetraisophthalic acid, octasodium salt | 7 | 2 | 6 | 58 | 66 | 71 | 76 |
| 5,5′,5″,5‴-[1,3,5,7-Naphthalenetetrayl-tetrakis(sulfonylimino)]tetra-1,2,3-benzenetricarboxylic acid, dodecasodium salt | 8 | 5 | 5 | 96 | 80 | 77 | 85 |

*Tests identified by code herein.
**Activity in wells, a serial dilution assay. Higher well number indicates higher activity. The serial dilutions are two-fold.

We claim:

1. A method of inhibiting the complement system in a body fluid which comprises subjecting said body fluid to the action of an effective complement inhibiting amount of a compound selected from those of the formula:

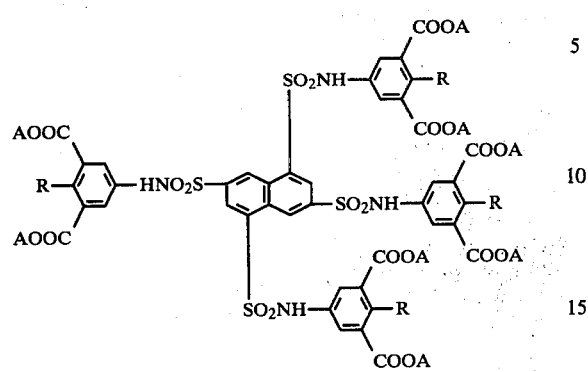

wherein R is selected from the group consisting of hydrogen and —COOA; and A is a nontoxic pharmaceutically acceptable cation salt, wherein the salt forming moiety is selected from the group consisting of alkali metal, an alkaline earth metal, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$).

2. A method of inhibiting the complement system in a warm-blooded animal which comprises administering to said animal an effective complement inhibiting amount of a compound selected from those of the formula:

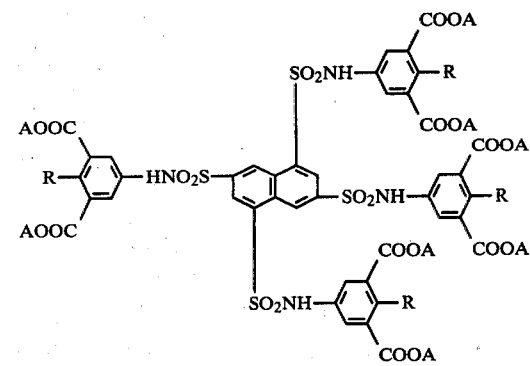

wherein R is selected from the group consisting of hydrogen and —COOA; and A is a nontoxic pharmaceutically acceptable cation salt, wherein the salt forming moiety is selected from the group consisting of alkali metal, alkaline earth metal, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$).

3. The method according to claim 1 or 2, wherein the compound is 5,5',5'',5'''-[1,3,5,7-naphthalenetetrayltetrakis(sulfonylimino)]tetraisophthalic acid, octasodium salt.

4. The method according to claim 1 or 2, wherein the compound is 5,5',5'',5'''-[1,3,5,7-naphthalenetetrayltetrakis(sulfonylimino)]tetra-1,2,3-benzenetricarboxylic acid, dodecasodium salt.

5. The method according to claim 2, wherein the compound is administered internally.

6. The method according to claim 2, wherein the compound is administered topically.

7. The method according to claim 2, wherein the compound is administered periodontally in the oral cavity.

8. The method according to claim 2, wherein the compound is administered intra-articularly.

9. The method according to claim 2, wherein the compound is administered parenterally.

* * * * *